US011213558B2

(12) United States Patent
Oroskar et al.

(10) Patent No.: US 11,213,558 B2
(45) Date of Patent: Jan. 4, 2022

(54) CBX EXTRACTION-ISOLATION PROCESS

(71) Applicant: Orochem Technologies Inc., Naperville, IL (US)

(72) Inventors: Anil Rajaram Oroskar, Oak Brook, IL (US); David W. House, Arlington Heights, IL (US); Kashif Shan, Colorado Springs, CO (US); Rajesh Kumar Gupta, Colorado Springs, CO (US)

(73) Assignee: Orochem Technologies, Inc., Naperville, IL (US)

( * ) Notice: Subject to any disclaimer, the term of this patent is extended or adjusted under 35 U.S.C. 154(b) by 0 days.

(21) Appl. No.: 15/981,520

(22) Filed: May 16, 2018

(65) Prior Publication Data
US 2018/0333446 A1    Nov. 22, 2018

Related U.S. Application Data

(60) Provisional application No. 62/507,448, filed on May 17, 2017.

(51) Int. Cl.
*A61K 36/00* (2006.01)
*A61K 36/185* (2006.01)

(52) U.S. Cl.
CPC ........ *A61K 36/185* (2013.01); *A61K 2236/50* (2013.01)

(58) Field of Classification Search
CPC ...................................................... A61K 36/00
USPC ........................................................ 424/725
See application file for complete search history.

(56) References Cited

U.S. PATENT DOCUMENTS

| 2,985,589 | A | 5/1961 | Broughton |
| 8,343,553 | B2 | 1/2013 | Hospodor |
| 9,034,395 | B2 | 5/2015 | Whittle |
| 9,044,390 | B1 | 6/2015 | Speier |
| 9,199,960 | B2 | 12/2015 | Ferri |
| 9,358,259 | B2 | 6/2016 | Hospodor |
| 10,413,845 | B1 | 9/2019 | Tegen et al. |
| 10,414,709 | B1 | 9/2019 | Tegen et al. |
| 2004/0033280 | A1 | 2/2004 | Whittle |
| 2005/0266108 | A1 | 12/2005 | Flockhart et al. |
| 2006/0167283 | A1 | 7/2006 | Flockhart et al. |
| 2008/0167483 | A1 | 7/2008 | Whittle et al. |
| 2012/0294887 | A1 | 11/2012 | Saunois et al. |
| 2015/0126596 | A1 | 5/2015 | Gutman et al. |
| 2018/0333446 | A1 | 11/2018 | Shan et al. |
| 2019/0144414 | A1 | 5/2019 | Erfurt et al. |
| 2019/0276420 | A1 | 9/2019 | Tegen et al. |

FOREIGN PATENT DOCUMENTS

| EP | 1536810 B1 | 8/2012 |
| WO | WO 2003/074144 A2 | 9/2003 |
| WO | WO 2004/026802 A1 | 4/2004 |
| WO | WO 2016/187679 A1 | 12/2016 |
| WO | 2017026897 A1 | 2/2017 |
| WO | WO 2017/194173 A1 | 11/2017 |
| WO | WO 2019/010419 A1 | 1/2019 |
| WO | WO 2019/173582 A1 | 9/2019 |

OTHER PUBLICATIONS

Brett Konen, "Why Ethanol Works So Well for Cannabis Extraction," Capna Labs, https://www.leafly.com/news/industry/ethanol-cannabis-extraction (Aug. 31, 2016).
HPLC-015 Application News—"Potency Testing in Cannabis Extracts Using a High Resolution Method with Cannabis Analyzer for Potency," Shimadzu Corporation (Feb. 2017).
HPLC-016 Application News—"Potency Testing in Cannabis Extracts Using a High Sensitivity Method with Cannabis Analyzer for Potency," Shimadzu Corporation (Feb. 2017).
HPLC-017 Application News—"Potency Testing in Cannabis Extracts Using a High Throughput Method with Cannabis Analyzer for Potency," Shimadzu Corporation (Feb. 2017).
Meyer et al., "Development of a rapid method for the sequential extraction and subsequent quantification of fatty acids and sugars from avocado mesocarp tissue," J Agric Food Chem., Aug. 27, 2008; 56(16)17439-45. doi: i 10.1021/jf18011322, Epub Aug. 5, 2008.
"Pros and Cons of Hemp Oil Extraction Techniques," Elixinol LLC, https://elixinolcbd.com/btogs/buyers-guide/16641671-pros-and-cons-of-hemp-oil-extraction-techniques (Mar. 12, 2015).
European Patent Office, International Search Report and the Written Opinion in International Application No. PCT/US2018/041096 (dated Oct. 31, 2018).
European Patent Office, International Search Report and the Written Opinion in International Application No. PCT/US2019/048160 (dated Jan. 24, 2020).

*Primary Examiner* — Michael V Meller
(74) *Attorney, Agent, or Firm* — Leydig, Voit & Mayer, Ltd.

(57) ABSTRACT

The present invention relates generally to improved methods for the extraction and isolation of cannabinoids from hemp. More particularly, the present invention relates to a series of extraction and isolation processes employed to selectively enhance recovery of non-psychoactive cannabinoids and the like, from *cannabis* materials and extracts, while removing undesirable naturally occurring components that may be present including colorants, carbohydrates, sugars and waxes, and the like, as well as contaminants that may be present in source materials including bactericides, fungicides, insecticides, plant growth regulators, environmental pollutants, and processing aids, and the like. The present invention further relates to an isolate obtained using a series of extraction and isolation processes that has extremely high cannabinoid content present in a stable, flowable liquid form that is essentially free of detectable levels of psychoactive cannabinol components.

17 Claims, 6 Drawing Sheets

CBX EXTRACTION-ISOLATION PROCESS

RELATED APPLICATIONS

This present application claims the priority of Unites States Provisional Patent Application Ser. No. 62/507,448 (filed on May 17, 2017) which is incorporated herein by reference in its entirety.

BACKGROUND

The present invention relates generally to improved methods for the extraction and isolation of phytocannabinoids from hemp. More particularly, the present invention relates to a series of extraction and isolation processes employed to selectively enhance recovery of non-psychoactive cannabinoids and the like, from *cannabis* materials and extracts, while removing undesirable naturally occurring components that may be present including colorants, carbohydrates, sugars and waxes, and the like, as well as contaminants that may be present in source materials including fungicides, insecticides, plant growth regulators, environmental pollutants, and processing aids and the like. The present invention further relates to an isolate obtained using a series of extraction and isolation processes that has extremely high phytocannabinoid content in a stable, flowable liquid form that is essentially free of detectable levels of psychoactive cannabinol components.

*Cannabis* and hemp have played important roles in most societies. The active ingredients in *Cannabis* species, including *Cannabis indica* and *C. sativa*, have been found to have medicinal properties including relief of symptoms of various diseases and conditions. The plant itself contains some 400 cannabinoids, each of which may have some therapeutic potential. Phytocannabinoids (cannabinoids) are compounds with 21 carbon atoms and carboxylic acids, analogs and transformation products of the 21-carbon compounds, the carboxylic acid forms being particularly prevalent in living cells and fresh plant product until environmental conditions decarboxylate them. Although the relative percentage of phytocannabinoids in *Cannabis* plants varies greatly with genetic and environmental factors, major constituents typically include tetrahydrocannabinol (THC), tetrahydrocannbinolic acid (THCA) and tetrahydrocannabinovarin (THCV), (collectively referred to as THC), cannabidiol (CBD), cannabidiolic acid (CBDA), cannabinol (CBN) along with minor constituents such as cannabichromene (CBC), cannabigerol (CBG), cannabigerovarin (GBGV), cannabinidiol (CBND), cannabicyclol (CBL), cannabichromevarin (CBCV), cannabidivarin (CBDV) and cannabigerol monomethyl ether (CBGM), collectively hereinafter being referred to as CBX actives, or phytocannabinoids.

Various historical methods of extraction which have been used to separate constituents of plant medicines and to produce enriched extracts include maceration, decoction, and extraction with aqueous and non-aqueous solvents, distillation and sublimation. Maceration (also known as simple maceration) is defined as the extraction of a drug in a solvent with daily shaking or stirring at room temperature. After a defined period the spent, solid material is separated from the solution (macerate). Variation on the method includes agitation of the macerate and the use of temperatures up to approximately 50° C. The method was formerly used for the preparation of tinctures and extracts from low-density plant materia medica, using various strengths of ethanol as the extraction solvent.

Decoction has been used since antiquity for the preparation of traditional medicines. In traditional Chinese medicine it is customary to place the quantity of herbs required for one day's treatment into a vessel to which hot or boiling water is added. The vessel is then raised to boiling point and allowed to simmer for 1½ hours (sometimes longer). The decoction so produced is allowed to cool, separated from solid particles, and the decoction is used as the dosage form for oral administration.

Maceration and decoction rely on a short diffusion path. Inactive constituents such as lecithins, flavonoids, glycosides and sugars may act to solubilize constituents which, in the pure state, are really soluble in the solvent. A disadvantage of maceration and decoction with water or low concentrations of ethanol is that a large quantity of inert material (ballast) that does not have therapeutic value is extracted. Ballast may consist of plant cell constituents including, but not limited to, fats, waxes, carbohydrates, proteins and sugars. A wide range of processes based on the use of non-aqueous solvents to extract the constituents from plants have been used in the prior art. The solvents employed may be miscible with water or water immiscible and vary in solvent power according to the concept of $E°$, which is familiar in the context of chromatography.

Traditionally, ethyl alcohol in various concentrations has been used to extract active substances from plant materials. Tinctures are alcoholic solutions produced in this way and tinctures of plant materials are described in all major pharmacopoeias. Ethanol extracts substances such as glycosides, flavonoids and alkaloid salts which are examples of classes of compound known to be biologically active. It also extracts considerable amounts of plant pigment, such as chlorophyll and carotenoids, which results in an undesirable taste and color. Since some of the organoleptic properties, clarity, taste etc., are negatively impacted by the chlorophyll, it should ideally be completely removed. By using higher alcoholic strengths lipid-soluble material may be extracted. Tinctures contain less ballast than macerates or decoctions, but are still complex mixtures of plant constituents. Where the presence of alcohol is not required the tincture can be evaporated to produce extracts. All pharmacopoeias contain liquid and solid extracts produced in this way.

Lipid solvents with a high $E°$ (solvent efficiency or solvency) value have been used to extract lipid soluble constituents from biomass. Examples are chlorinated solvents such as dichloromethane, chloroform and carbon tetrachloride, hexane, ether, fluorinated hydrocarbons and supercritical fluid extraction with agents such as carbon dioxide.

All of these approaches tend to extract all the THC and CBX components in like manner. However, there is growing evidence of the value of CBX materials themselves for use in the treatment and prevention of diseases and other medical ailments in humans and animals alike. Thus, these materials have great potential as therapeutic materials but are limited in use by the presence of psychoactive components of THC, including Δ8- and Δ9-tetrahydrocannabinols, analogs and derivatives, thereof. In addition, current Federal regulatory restrictions, despite many recent independent state initiatives to legalize the use of medically prescribed *cannabis* materials, are problematic for developing and distributing medicants with the psychoactive THC components present.

In addition, one of the desirable properties of a concentrated hemp oil rich in CBX components is the ability to remain in a stable, clear, liquid form. However, once the concentration of these components reach a potency of about 65-75%, the solubility limits are exceeded, and any shock to the system may result in premature precipitation and/or solidification of the concentrated extracts. However, it has been discovered that by removing the larger molecular hydrophobic species, such as waxes, that the stability of high potency CBX extracts can be significantly improved, enable easier processing, handling, transportation and storage versus conventional extracts.

Accordingly there is a need for better extraction processes that can not only extract high yields of desirable CBX materials, but can also isolate the CBX materials from psychoactive THC components, so that completely THC-free extracts can be obtained for therapeutic use.

SUMMARY

Disclosed herein is a series of processes for the isolation of phytocannabinoid components from a hemp extract. The series of processes includes optional and required process steps, depending on the starting material in hand and the particular process needing to be completed to remove undesirable components including chlorophyll, tannins, sugars, waxes, solvents and psychoactive components, and combinations thereof.

According to one embodiment of the present invention, one object of the present invention is a first extraction process employing the step of solvent extraction of plant components from a macerated hemp plant material, optionally followed by a distillation step to provide a first phytocannabinoid rich oil that is free from excess solvents; wherein said first extraction solvent is selected from a hydrophobic solvent when said plant material has a sugar:wax ratio exceeding 1:1; wherein said first extraction solvent is selected from a hydrophilic solvent when said plant material has a sugar:wax ratio less than 1:1.

A second object of the present invention is a second decolorization and dewaxing process employing the steps of diluting said first phytocannabinoid rich oil in a mixed Kb solvent to form a mixture and then treating said mixture by means of a series of at least one of a plurality of filtration steps to remove plant chlorophylls and waxes; wherein said first filtration step provides the effective removal of chlorophyll and said subsequent second, or alternatively third of said plurality of filtration steps provides the effective removal of wax components resulting in a second decolorized phytocannabinoid rich oil; wherein said first filtration step comprises passing said first phytocannabinoid rich oil through a filter media selected from activated carbon, carbon, clay, alumina, alumina-activated clay, cellulose, sand, silica, diatomaceous earth, crushed minerals including carbonate, granite and quartz, zeolites, synthetic materials including polymers, copolymers, resins, gels, and surface modified natural materials, and combinations thereof, layered constructs thereof and heterogenous mixtures thereof;

A third object of the present invention is a third THC removal process employing the step of treating said second decolorized phytocannabinoid rich oil by means of a THC extraction step; wherein said THC extraction step comprises passing said second decolorized phytocannabinoid rich oil through a fourth filter media; wherein said fourth filter is a mixture of at least two different particle size filter materials; wherein said third THC removal process results in the recovery of a third THC free decolorized phytocannabinoid rich oil; wherein said mixture includes a heterogenous mixture of two or more filter media or a layered construct thereof; wherein said filter media is selected from activated carbon, carbon, clay, alumina, alumina-activated clay, cellulose, sand, silica, diatomaceous earth, crushed minerals including carbonate, granite and quartz, zeolites, synthetic materials including polymers, copolymers, resins, gels, and surface modified natural materials, and combinations thereof, and heterogenous mixtures thereof;

A fourth object of the present invention is a fourth, optional sugar removal process employing the steps of a first, primary distillation of said third THC free decolorized phytocannabinoid rich oil, followed by a subsequent dilution step of the recovered distillate of said first primary distillation with a hydrophobic solvent; a subsequent precipitation step to remove precipitated sugars to produce an intermediate sugar-free extract; followed by a second, secondary distillation of said intermediate extract to produce a concentrated sugar and THC free decolorized phytocannabinoid rich oil;

A fifth object of the present invention is a fifth solvent reduction process employing the steps of first diluting said concentrated sugar and THC free decolorized phytocannabinoid rich oil using a first solvent in a primary series of rotovaping operations; followed by using a second solvent in a secondary series of rotovaping operations to produce a solvent-free, concentrated sugar and THC free decolorized phytocannabinoid rich oil; wherein said first and second series of said rotovaping operations each involves the step of heating and solvent removal under reduced atmospheric pressure until a point is reached in which no additional solvent condensation is observed.

A sixth object of the present invention is a process as described by any one or more combinations of embodiments of treatment steps as disclosed herein to obtain a concentrated sugar and THC free decolorized phytocannabinoid rich oil that is free of analytically detectable levels of pesticides, fungicides and heavy metals.

A seventh object of the present invention is a process as described by any one or more combinations of embodiments of treatment steps as disclosed herein to obtain a stable, concentrated sugar and THC free decolorized phytocannabinoid rich oil extract that contains not less than 85 or alternatively not less than 80 wt./vol. % of CBX materials selected from cannabidiol (CBD), cannabidiolic acid (CBDA), cannabinol (CBN), cannabichromene (CBC), cannabigerol (CBG), cannabigerovarin (GBGV), cannabinidiol (CBND), cannabicyclol (CBL), cannabichromevarin (CBCV), cannabidivarin (CBDV) and cannabigerol monomethyl ether (CBGM), and other hemp plant essential oils; wherein levels of tetrahydrocannabinol (THC), tetrahydrocannbinolic acid (THCA) and tetrahydrocannabinovarin (THCV) are all below 0.3 wt./vol. %, or alternatively below 0.1 wt./vol. %, or yet alternatively below 0.01 wt./vol. %.

An eighth object of the present invention is isolation of a stable, concentrated sugar and THC free decolorized phytocannabinoid rich oil extract obtained by means of one or more of the process steps disclosed herein, wherein said phytocannabinoid rich oil is free of visible chlorophyll and free of measurable quantities of wax; and is in the form of a stable, homogenous solution free of suspended solids and free of analytically detectable levels of pesticides, fungicides and heavy metals.

DESCRIPTION

Generality of Invention

Figure 1:
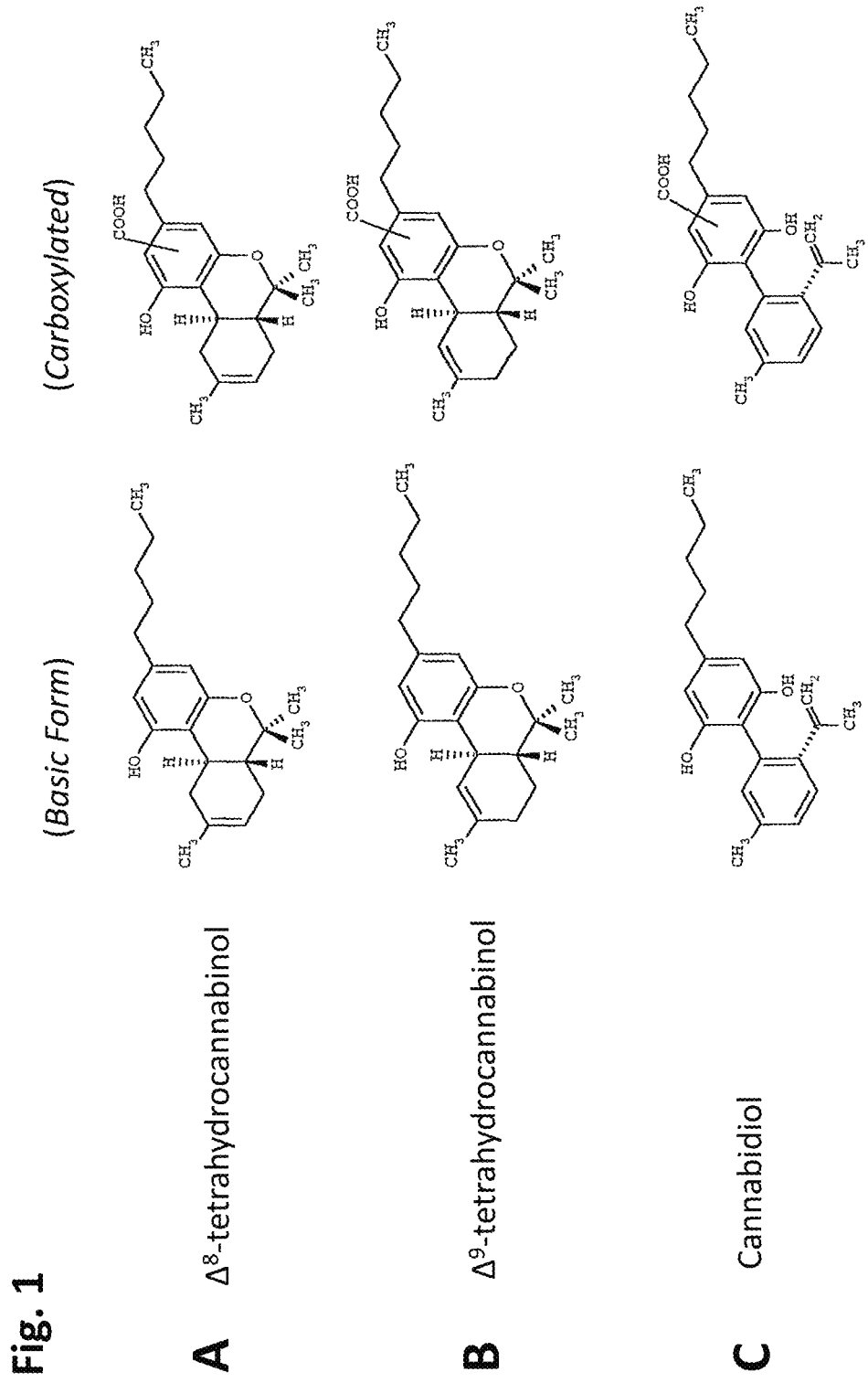
FIG. 1 shows the similar chemical structures of various *cannabis* essential oil components.

This application should be read in the most general possible form. This includes, without limitation, the following:

References to specific techniques include alternative and more general techniques, especially when discussing aspects of the invention, or how the invention might be made or used.

References to "preferred" techniques generally mean that the inventor contemplates using those techniques, and thinks they are best for the intended application. This does not exclude other techniques for the invention, and does not mean that those techniques are necessarily essential or would be preferred in all circumstances.

References to contemplated causes and effects for some implementations do not preclude other causes or effects that might occur in other implementations.

References to reasons for using particular techniques do not preclude other reasons or techniques, even if completely contrary, where circumstances would indicate that the stated reasons or techniques are not as applicable.

Furthermore, the invention is in no way limited to the specifics of any particular embodiments and examples disclosed herein. Many other variations are possible which remain within the content, scope and spirit of the invention, and these variations would become clear to those skilled in the art after perusal of this application.

Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The use of weight and volume measures include the English and metric system, "lb." referring to pounds, including dry weights, "gm" and "kg" corresponding to gram and kilogram weights, including liquid and dry weights, and "mL" and "L" corresponding to milliliter and liter volumes. In addition, percentages include weight percentages, expressed as "wt. %" and volume percentage, expressed as "vol. %", as well as mixed measurements when a solid material is added to a liquid, which may be expressed either as a weight/weight ratio or weight % as "wt./wt. %" or "w/w", or conversely expressed as a weight/volume ratio as weight/volume % or "wt./vol. %" or "w/v". Alternatively, when liquid materials are combined, the mixture may be expressed either as a ratio based on either weight or volume, such as weight:weight or volume:volume, and if not expressly indicated, generally refers to the ratio of liquid volumes as the default.

Concentration terms include weight % of an active expressed in terms of parts per million (ppm), wherein 1.0 wt. % is equivalent to 10,000 ppm, or parts per trillion (ppt), wherein 0.001 wt. % is equivalent to 10,000 ppt, respectively.

Read this application with the following terms and phrases in their most general form. The general meaning of each of these terms or phrases is illustrative, not in any way limiting.

DETAILED DESCRIPTION

The present inventors have developed a multistep but versatile process that maximizes the recovery of phytocannabinoids (CBX) from hemp, while removing undesirable colorants (such as chlorophylls, tannins, and the like), waxes (terpenes, gums, resins and similar high molecular weight hydrocarbons), sugars (sucrose, galactose and other similar carbohydrates) and other contaminating materials present (such as pesticides, fungicides and biocides). Accordingly, the multistep process produces an essentially THC-free phytocannabinoid rich oil that is free of trace impurities, solvents, extractants and other processing chemicals, and that has the characteristic of being in a flowable, storage stable liquid concentrate form with greater than 85 wt. % of CBX components present for use in medicinal and pharmaceutical formulations.

Extraction Process

FIG. 1 shows the similar chemical structures of various *cannabis* essential oil components, the two psychoactive delta-8 ($\Delta^8$) and delta-9 ($\Delta^9$) tetrahydrocannabinol in both their basic and carboxylated form, compared to cannabidiol in its basic and carboxylated form. It is noted that the overall structures, chemical substituents (moieties) and molecular weights of the various compounds are very similar in nature, suggesting that extraction or attempts to isolate one from the other, particularly in mixtures containing a multitude of additional and similar components differing only slightly in chemical structure, presents a difficult challenge. Nevertheless, the present invention, illustrated by means of the inventive embodiments disclosed herein that can be used in proscribed process steps for extraction and isolation of the desired phytocannabinoids, provides a means to tailor the extraction and removal of undesirable materials, and isolation of the CBX components with a remarkably high degree of recovery and in a high state of purity.

Figure 2:
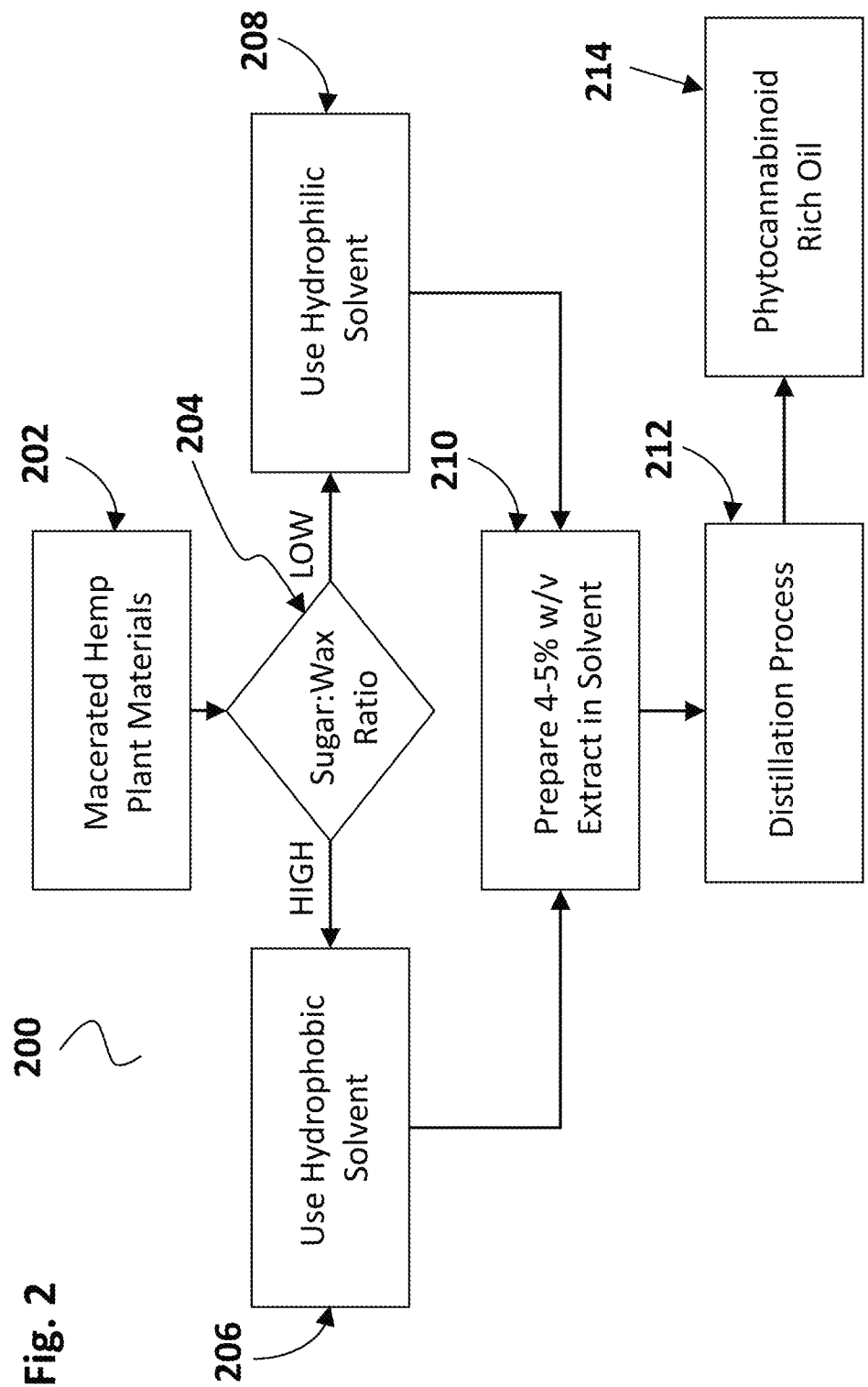
FIG. 2 shows a first extraction process beginning with macerated hemp plant materials employing a selected solvent that is removed by distillation to provide a phytocannabinoid rich oil precursor.

FIG. 2 shows an embodiment of an optional first extraction process, being a hemp extraction process 200 beginning with macerated hemp plant materials 202 subject to an extraction step using a selected solvent that is removed by distillation to provide on recovery, a phytocannabinoid rich oil 214. Hemp materials are selected from *Cannabis sativa, Cannabis indica* and *Cannabis ruderalis* plants, although the former two are generally selected owing to their higher CBD content. The typical ratio of tetrahydrocannabinols (THC) to cannabinoids (CBX) in most *Cannabis* varieties of both types are similar (averaging about 200:1), but strains of both exhibiting lower THC ratios with higher CBX content are preferred. Avidekel, a medical marijuana strain developed in Israel, has a very low content of THC but a high content of CBX, limiting its recreational value but maximizing medical effect, and is thus a good candidate as well. [See Halverson, Nic (Jul. 6, 2012) "Marijuana That Doesn't Get You Stoned", Discovery Channel, Discovery Communications, LLC. Retrieved Jan. 23, 2014.] Most preferred are variants with the lowest THC:CBX ratio and highest CBX concentration, including fiber hemp strains of *Cannabis sativa* L. Different parts of the plant, including leaves, flowers, seeds and seed pods and stems can be utilized. Generally a first step following harvesting of the plant materials is a drying step to remove excess moisture and reduce the water content of the solid materials to a point sufficient to deter mold and mildew growth, and slow degradation processes. The dry plant materials are preferably maintained in an unaltered and dry state (although they may be compressed and compacted for ease and efficiency in handling, transport and storage) until just prior to the start of processing, of which the first step is to macerated the materials to produce a fine uniformly sized granulate or powder, the maceration step acting to break down plant ligature, rupture plant cells and release cellular materials, compounds and components, rendering the material into a form having a high surface area accessible for the subsequent solvent extraction step.

In a second extraction step, the preferred first extraction solvent to be selected depends on the sugar:wax ratio of these components present in the original macerated hemp material to be processed, as determined by analytical evaluation of a sample thereof. Sugars, being single and complex carbohydrates, are hydrophilic in nature, and thus are fairly water and alcohol soluble, while waxes are hydrophobic in nature and essentially insoluble in water and only sparingly soluble in alcohol. Accordingly, for hemp materials having an initially high sugar:wax ratio, the preferred extraction solvent is selected from a more hydrophobic solvent, such as an alkane, or substituted alkane derivative. Suitable hydrophobic solvents include, for example, but are not limited to, acetonitrile, benzene, butanols, chloroform, cyclohexane, 1,2-dichloroethane, dichloromethane, diethyl ether, N,N-dimethylformamide, ethyl acetate, hexane, methylbutyl ketone, methylcyclohexane, pentane, propanols, tetrahydrofuran, toluene, and xylene and the other solvents and solvent systems known to the art to have medium to relatively high Kauri-butanol value ("Kb value"). The Kb value is an international, standardized measure of solvent power for a hydrocarbon solvent, and is governed by a ASTM standardized test method, ASTM D1133-10 entitled "Standard Test Method for Kauri-Butanol Value of Hydrocarbon Solvents." The result of this test is a scaleless index, with a higher Kb value meaning the solvent is more aggressive or active in the ability to dissolve certain materials. Mild solvents have low scores in the tens and twenties; powerful solvents like chlorinated solvents and naphthenic aromatic solvents have ratings that are in the low hundreds. The choice of solvent also depends on the relative toxicity and allowable maximum residual concentrations that are acceptable for later intended usage, such as for example, whether the resulting CBX materials are to be formulated into USP (United States Pharmacopeia) compliant products.

In one embodiment of the invention, a medium alkyl chain length non-aromatic saturated hydrocarbon such as pentane, hexane, heptane or octane, or a combination thereof, is suitable as a first extraction solvent when treating hemp materials with a high sugar:wax ratio, as a first extraction with a higher Kb value solvent will favor hydrophobic materials, leaving sugars and more water soluble materials behind (unextracted).

In an alternative embodiment of the invention, when the hemp material has a low sugar:wax ratio, a first extraction solvent is preferred that is more hydrophilic in nature, or has a lower Kb value, examples including, but not limited to, water, low alkyl chain length alkanols such as methanol, ethanol, propanol and butanol, and isomers thereof, acetone, alkyl diols, glycerol's and the like. By employing a more hydrophilic solvent in this instance, waxes present in the hemp material are preferentially left unextracted, having correspondingly lower solubility's in low Kb solvents and more hydrophilic or water-miscible solvents.

For other embodiments of the invention where the sugar:wax ratios are comparable, either type of solvent system can be selected as disclosed herein, or alternatively, mixtures of solvents representative of both hydrophilic and hydrophobic solvents of low to medium Kb values can suitably be employed in the first extraction step of the present invention, provided they are compatible, miscible with one another, and produce an result at least equivalent to that produced by using the separate solvents alone.

To perform the various embodiments of the first extraction, the macerated hemp plant materials are intimately mixed together with the selected solvent in any desired ratio selected from between 1:2 to 2:1 (v/v of plant material dry volume:solvent volume), or alternatively between 1:3 to 3:1, or alternatively between 1:4 to 4:1, or yet alternatively between 1:5 to 5:1. Generally, a lower ratio having greater solvent volume present is desirable to insure sufficient contact and extraction of the largest amount of material from the plant material, although this results in larger solvent extraction volumes per unit volume of initial plant material. Accordingly, in some embodiments, a preferred ratio is between 1:2 to 1:8, or alternatively between 1:3 to 1:7, or alternatively between 1:4 to 1:6, or alternatively between 1:4 and 1:5.

To achieve suitable extraction efficiencies, the macerated plant materials are thoroughly physically mixed in a suitable extraction vessel with the first extraction solvent selected, for a time sufficient to insure at a minimum that the plant materials are completely wetted and saturated by the solvent, and for an additional time in a wetted contact condition to reach a near equilibrium extraction stage, generally achievable at an industrial sized scale, but dependent on the nature of the macerated materials, their particle size and particle size distribution, choice of solvent, extraction ratio, and mechanical factors including the mixing energy, turnover rate, temperature, and the like. In example embodiments, processing of finely ground and macerated hemp materials using either ethanol or hexane solvent as the first extraction solvent was complete within about 180 minutes, longer extraction times up to about 4 hours also being acceptable, but generally not producing significantly greater degrees of extraction.

As shown in FIG. 2, a hydrophobic solvent 206 is selected for use in the case of a high sugar:wax ratio (High, 204) being determined from analysis of the macerated hemp plant materials, while a more hydrophilic solvent 208 is selected in the case of a low ratio (Low, 204).

Following the first extraction step, the spent (extracted) plant material is generally precipitated, pressed, screened or centrifuged to separate solids from the extraction solvent. At this stage, typical extraction efficiencies, dependent on the plant:solvent ratio of course, produce extracts having between 1 to 10 wt./vol. % (w/v) of extract composed of lipids, terpenes, and CBX materials. In the embodiment shown in FIG. 2, an extraction efficiency of between 4-6 wt./vol. % is shown, being a typical yield from a first extraction step. Once a clear and solids-free solvent extract 210 is recovered from the spent plant material, the solvent extract can then be distilled by a suitable distillation process 212 to remove excess solvent, producing a phytocannabinoid rich oil 214. Generally, the distillation process removes sufficient solvent to concentrate the materials about 10 to 20 fold (10×-20×), producing a phytocannabinoid rich oil (PCR oil) having from between about 40 to 60 wt./vol. % of CBX components present, along with other undesirable materials including THC and residual sugars and waxes.

Multiple types of "distillation" processes for performing the distillation steps disclosed as embodiments of the present invention are suitable for use, including for example, but not limited to simple distillation, accelerated solvent recovery distillation, column distilling, vacuum and vacuum steam distillation, stirred reactor unit distillation and molecular distillation methods, which use one or more of a combination of heating, cooling, agitation, vacuum and recirculation means to enhance solvent removal from a starting material and to safely recover distillates (solvents) for re-use, recycling and/or disposal.

Suitable distillation apparatus for performing distillation steps disclosed as embodiments of the present invention are commercially available in suitable size capacities for industrial processing, including for example, but not limited to, Eden Coldfinger™ and vacuum steam distillers, available from Eden Labs, LLC, 309 S Cloverdale St, Seattle, Wash. 98108, USA, the SRXC series automated chemical distillation columns, available from IST Pure Ltd., 4160 Indus triel Blvd., Laval (Qc), Canada, H7L 6H1, and the Wipe-Film and Fractional Distillation column units available from Pope Scientific, Inc., 351 N. Dekora Woods Blvd., P.O. Box 80018, Saukville, Wis., 53080 USA.

Decolorization and Dewaxing Process

Figure 3:
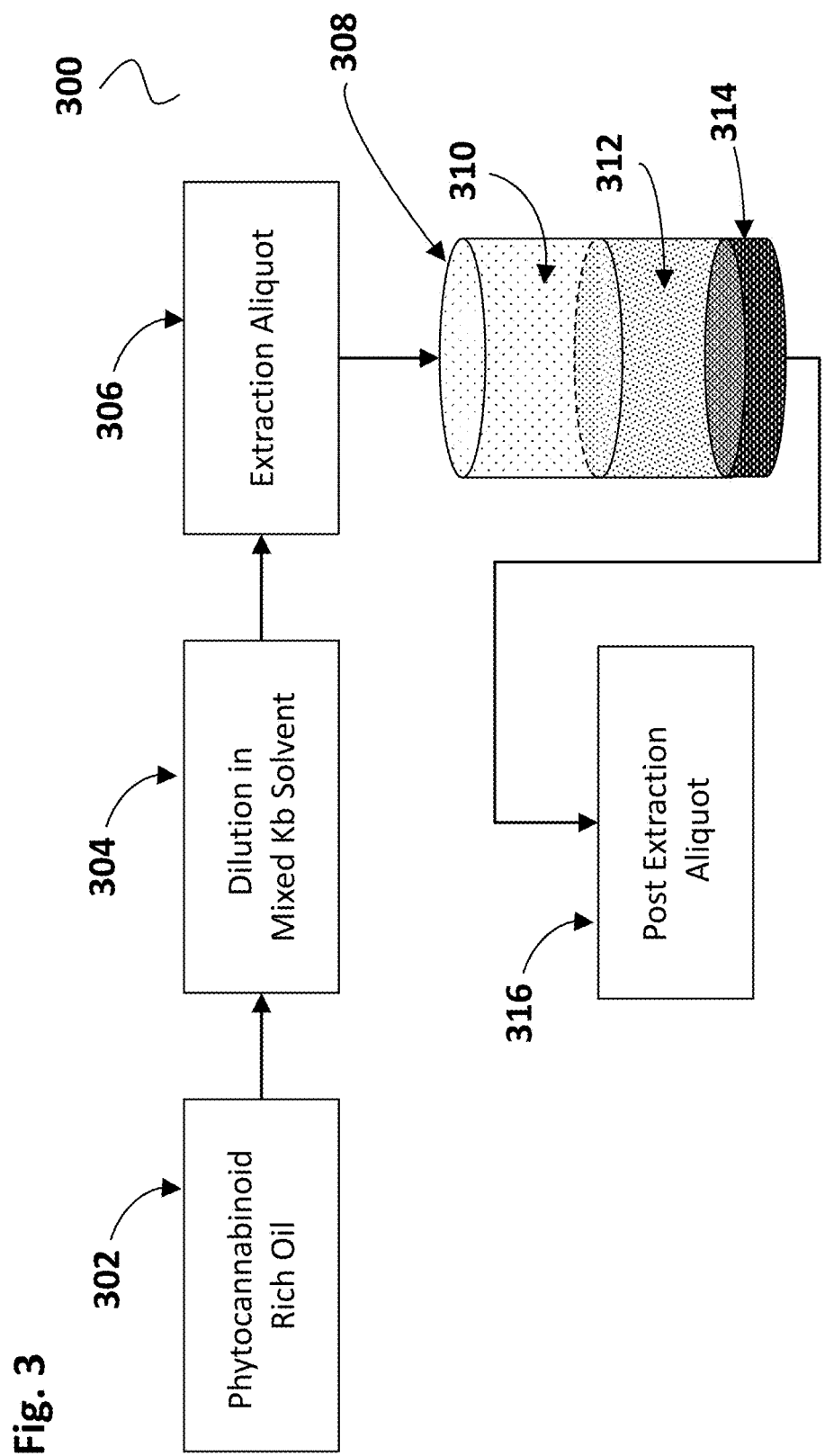
FIG. 3 shows a second decolorization and dewaxing process beginning with a phytocannabinoid rich oil precursor and ending with a post extraction oil with plant chlorophylls and waxes removed.

FIG. 3 shows an embodiment of an optional second treatment process, being a decolorization and dewaxing process 300, illustrated as a series of steps beginning with a phytocannabinoid rich oil precursor 302 or the distilled extract resulting from the first extraction process described hereinabove in the discussion of FIG. 2. In embodiments of a second treatment process 300, the PCR oil is first diluted into and dissolved by a low Kb solvent that retains the phytocannabinoids in solution but which aids in the subsequent removal of more hydrophobic components such as wax. In one embodiment, a PCR oil 302 with a suitably high level of CBD present at about 50 wt./vol. % is diluted by a quantity of mixed 80:20 (v/v) ethanol and water sufficient to reduce the CBD concentration at least by a factor of two, and up to a factor of about 20, resulting in a reconstituted PCR solution with between 2 to 25 wt./vol. %, or alternately between 2.5 to 20 wt./vol. %, or alternatively between 3 to 10 wt./vol. %, or yet alternatively between 4 to 5 wt./vol. %. Following dilution of the PCR oil by the solvent of choice in step 304, an aliquot of the diluted extract 306 is injected into a filtration column 308 that has at least one first filtration media 310 and optionally a second filtration media 312 that are retained on column, optionally by a column media retention aid 314, being for example, but not limited to, a screen or filter or similar means to prevent the filtration media from being washed from or ejected from the filtration column 308. Following treatment of a first extraction aliquot 306 by means of passing it completely through 308, a post extraction aliquot 316 is obtained. In an alternative embodiment, the filtration column 308 can be prewetted with a sufficient volume of the dilution solvent used in step 304, or any other suitable, miscible solvent or solvent mixture, to facilitate filtration, ease the first wetting of the filtration media, and prevent gas bubbles or inclusions from forming inside the filtration column. In yet another embodiment, the process can be made continuous, rather than done in batch mode, by introducing or injecting a continuous flow of the extraction aliquot 306 onto the filtration column 308. Generally, when operating in either a batch or a continuous flow mode, the selection of filtration parameters, including relative solvent:column media volume ratio, injection speed, contact time and temperature, are selected to provide the highest degree of desired filtration under the shortest contact times for efficiency of operation.

In an example embodiment employing the decolorization and dewaxing process 300, an initial PCR oil was diluted in an 80:20 (v/v) ethanol:water solution to produce an approximate 4 wt./vol. % CBX concentrated solution. This solution was then injected onto a mixed media filtration column 308 having a first and second filtration media 310 and 312, respectively, being a mixture of a first finely ground and secondly coarsely ground activated carbon particles, of roughly equal volumes, intimately mixed together to form a heterogenous mixed filtration media. In related embodiments of the invention, a wide variety of suitable filtration media exist that are suitable for use, including, but not limited to clay, alumina, alumina-activated clay, cellulose, sand, silica, diatomaceous earth, carbon and activated varieties thereof, crushed minerals such as carbonate, granite and quartz, zeolites, and materials having suitable absorptive natures with respect to the material to be retained, as well as synthetically derived materials, including, but not limited to polymers, copolymers, resins, gels, and modified natural materials, which are commercially available and can generally be selected for use depending on the filtration solvent to be used and the material to be retained. In this example embodiment, activated carbon was employed in a fine form corresponding to a particle size retained on an 80×325 US Mesh, and a slightly coarser form corresponding to a US Mesh size of 12×40, layered into two separate layers, with an optional media retention 314 aid being a standard filter paper disc as shown but illustrated as column media retention aid 314. In related embodiments, the finer and coarser media may be mixed together to form a heterogenous mixture, used instead of or in replacement of one of the media layers disclosed above.

Activated carbon materials are available from a wide variety of commercial sources and are suitable for use herein, being obtained from coconut shells, wood and coal sources that are "activated" by partial combustion and other modification processes to create highly porous, extremely high available surface area absorbents. In general, any commonly available commercial source of these materials are suitable for use in embodiments of the present invention, suitable examples include, but are not limited to granular TOG-LG and Centaur grades, available from Calgon Carbon Corporation, 3000 GSK Drive, Moon Township, Pa. 15108, USA, coconut shell and wood activated carbons from Carbon Activated Corporation, 2250 S Central Avenue, Compton, Calif. 90220, USA, "GC" series liquid phase activated carbon, available from General Carbon Corporation, 33 Paterson Street, Paterson, N.J. 07501, USA, and TIGG "5D" series liquid phase activated coconut shell carbon filtration media, available from TIGG, a division of Spencer Turbine, Pa. Corporate Headquarters located at 1 Willow Avenue, Oakdale, Pa. 15071, USA. The various granular activated carbon (GAC) materials are available in a fairly large range of mesh or particle size ranges, from extremely fine sizes (high grating no.) to coarse sizes (lower grating No.s.). In related embodiments of the present invention, the choice of mesh or particle size is driven mostly by surface area considerations, and packing efficacy, as two or more particle size range materials can often be mixed to produce a tighter filtration bed, the smaller particles tending to fill the voids between larger particles, the mixed beds providing an advantage with greater solvent flow-through rates and porosity than single mesh size beds of comparable total surface area. In general, embodiments using filtration columns made with single finer mesh sizes are less easily wetted and tend to have lower solvent flow-through rates, being less porous, and prone to higher back pressures.

Accordingly, in some embodiments, a mixed or heterogenous filtration media composed of two significantly distinct mesh size or particle size distribution of the same filter material is preferred over use of a single mesh size or homogenous filtration media.

In other embodiments, the filtration step can be completed using a single filtration media and process step, or by subsequent filtration steps repeated on the extracted liquid aliquot in succession on the same or a second, different filtration media, as required to remove a desired amount of colorized species (chlorophylls, phytols, tannins, pigments and other "colorants") and/or a desired amount of wax and the like. In further related embodiments, the filtration step can be completed using any desired mixture of filtration media, or multiple filtration steps using one or more columns containing the same or different media, selected accordingly to remove one or more desired materials or contaminants, for example, a first filtration step with a filtration media selected having a high absorptivity and/or selectivity for colorants, followed by a second filtration step with a second filtration media selected having a high absorptivity and/or selectivity for waxes and other hydrophobic, long chain or high carbon number materials desired to be removed.

Following the decolorization and dewaxing process 300, one example embodiment utilizing a filtration step 308 employing a 50:50 v/v mixture of Calgon Carbon TOG-LG and Centaur 20×50 granulated activated carbon, produced an essentially chlorophyll- and wax-free extract having approximately 3.5 wt./vol. % PCR oil present in the post filtration solvent (80:20 ethanol/water) having an enriched CBD content in the PCR oil of about 70 wt. % (wt./wt. %), resulting in an amplification of about 20% in CBD enrichment compared to the prefiltered extraction aliquot 306, which started with an approximately 50% CBD content in the PCR oil present at about 4 wt./vol. % following dilution of the PCR oil obtained from a first extraction process 200.

In a related embodiment, higher molecular weight molecules such as chlorophyll (~1000 Da), which are much larger than cannabinoids and terpenes (~300-400 Da), can alternatively be removed by employing a microfiltration process, which involves passing the concentrated CBX extract through a 500-900 Da pore size filter, such as for example, but not limited to, a Millipore Biomax PB membrane or Ultracel PLC membrane with 1 kDa cutoff, available from the Millipore Corporation, Billerica, Mass. 01821, U.S.A. In a further embodiment, this microfiltration step can be performed prior to, or after, the disclosed extraction step for removing colorants and waxes according to one or more of the embodiments above.

THC Removal Process

Figure 4:
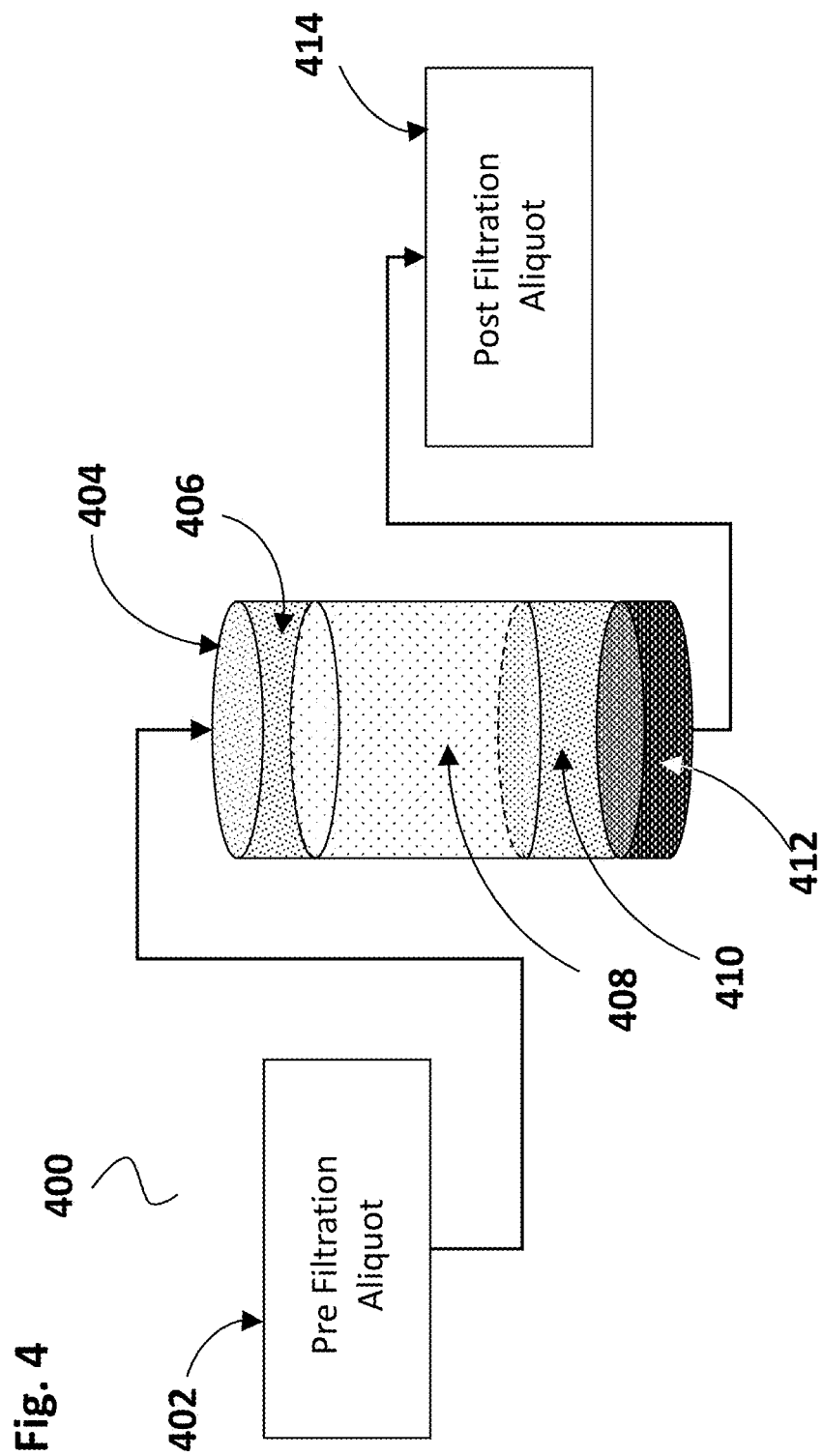
FIG. 4 shows a third extraction process to remove the active THC components from a phytocannabinoid rich oil intermediary.

FIG. 4 shows an embodiment of an optional third extraction process, being a THC removal process 400 employed to remove the active THC components from a phytocannabinoid rich oil intermediary material, or one obtained as a result of one or more inventive embodiments of a second extraction process as described hereinabove. In this embodiment, the THC removal process 400 involves subjecting a prefiltration aliquot 402 of a PCR oil solution to a filtrating step employing a filtration column 404. In the embodiment shown in FIG. 4, filtration column 404 contains layered media, a first filtration media 406, a second filtration media 408 and a third filtration media 410, retained by an optional column media retention aid 412. Following treatment of an aliquot of material 402 by passing through filtration column 404, a post filtration aliquot 414 is obtained that is desirably essentially free of THC and THCA components, or reduced sufficiently in degree so as to be essentially undetectable, or below about 0.01 wt./vol. % in the post filtration material 414.

In related embodiments, the filtration column 404 can be used with a single filtration media 406 alone, or alternatively with said first and a second filtration media 408, or alternatively with said first, said second and a third filtration media 410. In additional embodiments, the filtration column 404 can be used with a single heterogenous mixture of multiple filtration media selected from 406, 408 and 410, singly, dually and triply, or combinations thereof.

In an example embodiment, a PCR solution containing about 2 wt. % of THC present, with about 3.5 wt./vol. % PCR oils (having a CBD content of about 75 wt. %) in an 80:20 ethanol/water solution was treated using a three-stage filtration step as shown in FIG. 4, where the first and third filtration media, 406 and 410, respectively, were layers of packed Centaur grade granular activated carbon, and the intermediary or second filtration media 408 was TOG GAC. After treatment by passing through filtration column 404, the post filtration aliquot was analyzed and found to have a content of about 3.4 wt./vol. % PCR oil with a CBD content of about 75 wt. %, but was notably absent of any detectable amount of THC or THCA. Accordingly, embodiments of the THC removal process 400 employing activated carbon as a filtration media are extremely effective at removing THC (and THCA) without appreciably reducing or removing significant amounts of desired CBX materials. In this present embodiment, only a reduction of approximately 0.1 wt./vol. % of total PCR oil was observed, this either being lost on the column or due to wetting loss on column, some being accounted for within the statistical error. In further embodiments, extraction and filtration columns as employed herein, can optionally be rinsed after use to recover additional material, or used in successive filtration steps to minimize wetting loss and aid in the recovering of additional retained material, if that is desired.

In another embodiment, the phytocannabinoid rich oil intermediary material disclosed as the starting material in this particular step to remove THC can be pretreated by activation or heating the concentrated oil for 2-4 hours at a temperature of about 330° F. (165° C.) in order to convert any THCA present into THC, which is more easily removed by means of the extraction process disclosed herein than its precursor.

To quantitate the amount of residual THC and THCA present, the analytical method of choice to test the example PCR-hemp oils obtained using the present inventive embodiments is High Performance Liquid Chromatography (HPLC). The preferred test method is based on a reverse-phase C18 column being able to separate and measure individual components of the PCR hemp oil. To ensure that the THC and THCA have been completely removed from the PCR hemp oil, its limit-of-quantitation (LOQ) and the limit-of-detection (LOD) have been determined to be 0.1% and 0.01%, respectively. The test results for THC/THCA in the PCR hemp oil product data sheet may range from "Absent" (representing levels that cannot be detected, <0.01%), to "0.01%-0.1%" since accurate quantitation in that range is improbable. The THC and THCA levels will never exceed 0.1% in the PCR hemp oil as a result of the manufacturing process disclosed herein, so the final levels of THC and THCA as specified in the product data sheet is at or below the detection limit.

In related embodiments, other filtration media can be employed in the filtration column 404, including for example, but not limited to, clay, alumina, alumina-activated clay, alumina, cellulose, sand, silica, diatomaceous earth, carbon and activated varieties thereof, crushed minerals such as carbonate, granite and quartz, zeolites, and materials having suitable absorptive natures with respect to the material to be retained, as well as synthetically derived materials, including, but not limited to polymers, copolymers, resins, gels, and modified natural materials, which are commercially available and can generally be selected for use depending on the filtration solvent to be used and the material to be retained.

Sugar Removal Process

Figure 5:
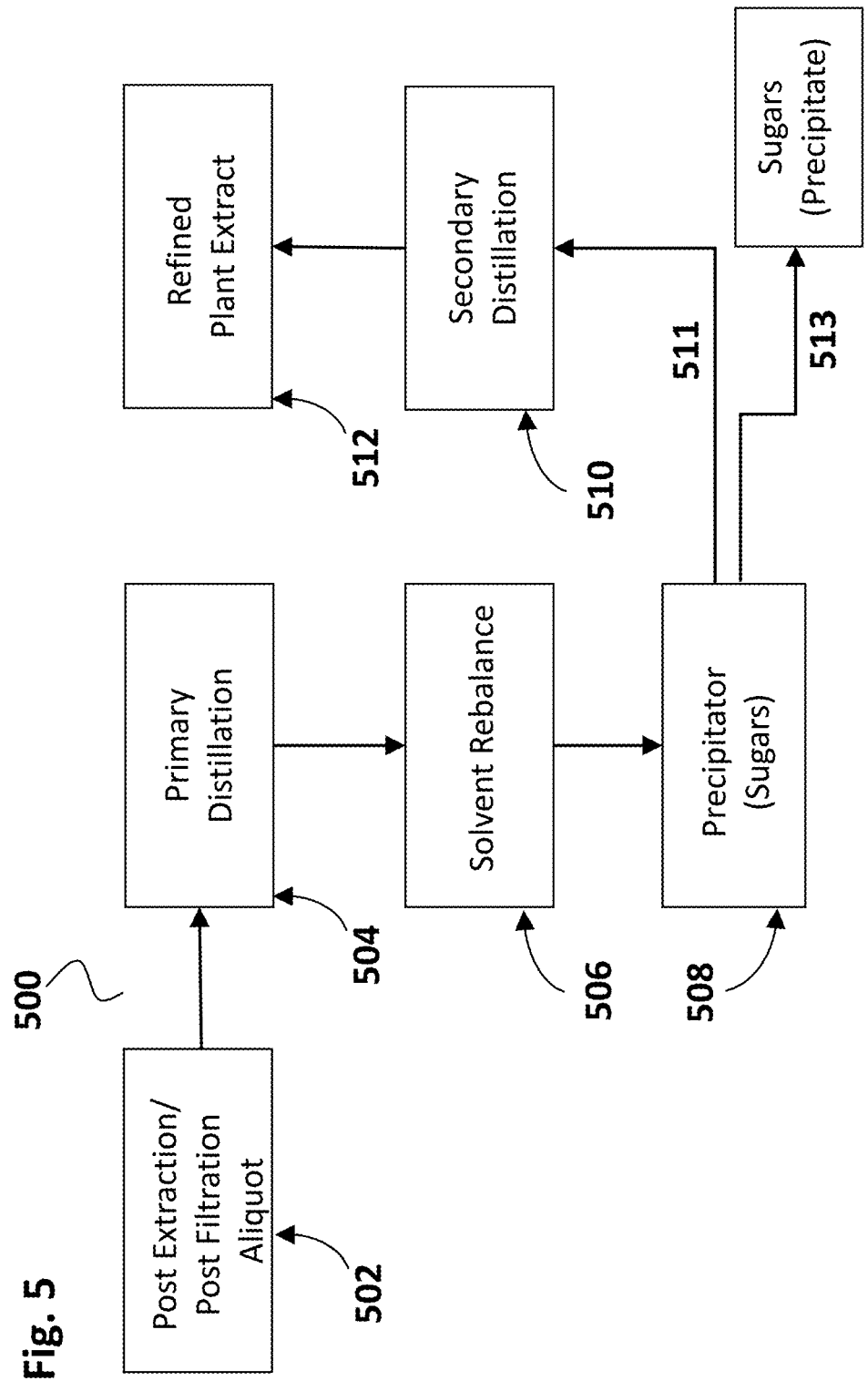
FIG. 5 shows a fourth process to remove sugars by precipitation from a phytocannabinoid rich oil intermediary using dual distillation steps after reconstitution in a selected solvent.

FIG. 5 shows an embodiment of a fourth, optional process, being a sugar removal process 500 to remove sugars and related water-soluble carbohydrates from a phytocannabinoid rich oil intermediary using dual distillation steps, a primary distillation step 504 and a secondary distillation step 510 after reconstitution in a selected hydrophobic and low E° solvent or solvent mixture in a solvent rebalance step 506 and a precipitation process conducted in an intermediary precipitator step 508.

In a first step of one embodiment of a sugar removal process 500, an aliquot of PCR oil obtained from a previous THC removal step as a post filtration aliquot 502 is subject to a distillation step to remove residual water and ethanol present from a previous treatment step. After a primary distillation 504, the residual distillate remaining is dissolved in a suitable solvent, in one example embodiment being a 1:7 ethanol:hexane (v/v) solvent mixture, in a solvent rebalance step 506. After agitation and dispersion of the oily distillate into the fresh solvent mixture, the mixture is optionally allowed to settle or in another optional embodiment, introduced into a precipitator 508, where it is allowed to cool in order to enhance the precipitation of sugars and other carbohydrates that have limited solubility in the high alkane content solvent. In alternative embodiments of a precipitation step, a small seed crystal or other insoluble high surface area catalyst can be introduced to the precipitator 508 to initiate crystallization and increase the yield of precipitated sugars. In yet another related embodiment, the disclosed precipitation step can be performed in the same vessel used in the preceding primary distillation step 504, by means of introducing the rebalancing solvent and optionally employing the use of cooling or introduction of a seed crystal or catalyst to induce precipitation of sugars. Following precipitation, the precipitated materials 513 are removed or decanted from the mother liquor, optionally rinsed with a cooled aliquot of the rebalancing solvent to flush out remaining liquid, and then separated from the process for disposal or other use. Following the optional precipitation step 508, a secondary distillation step 510 is employed for the purpose of removing the solvent, and in particular the alkane component of the solvent, from the resulting, de-sugared PCR oil, resulting in a refined plant extract 512 that is high in PRC oil content with a high percentage of the oil being the desired CBX components, now free from sugar and other carbohydrate impurities. In this embodiment of the disclosed precipitation step 508, isolated sugar precipitate 513 is separated and recovered from the precipitator, while decanted extract 511 is then subject to a secondary distillation step 510 as described above.

Solvent Removal Process

Figure 6:
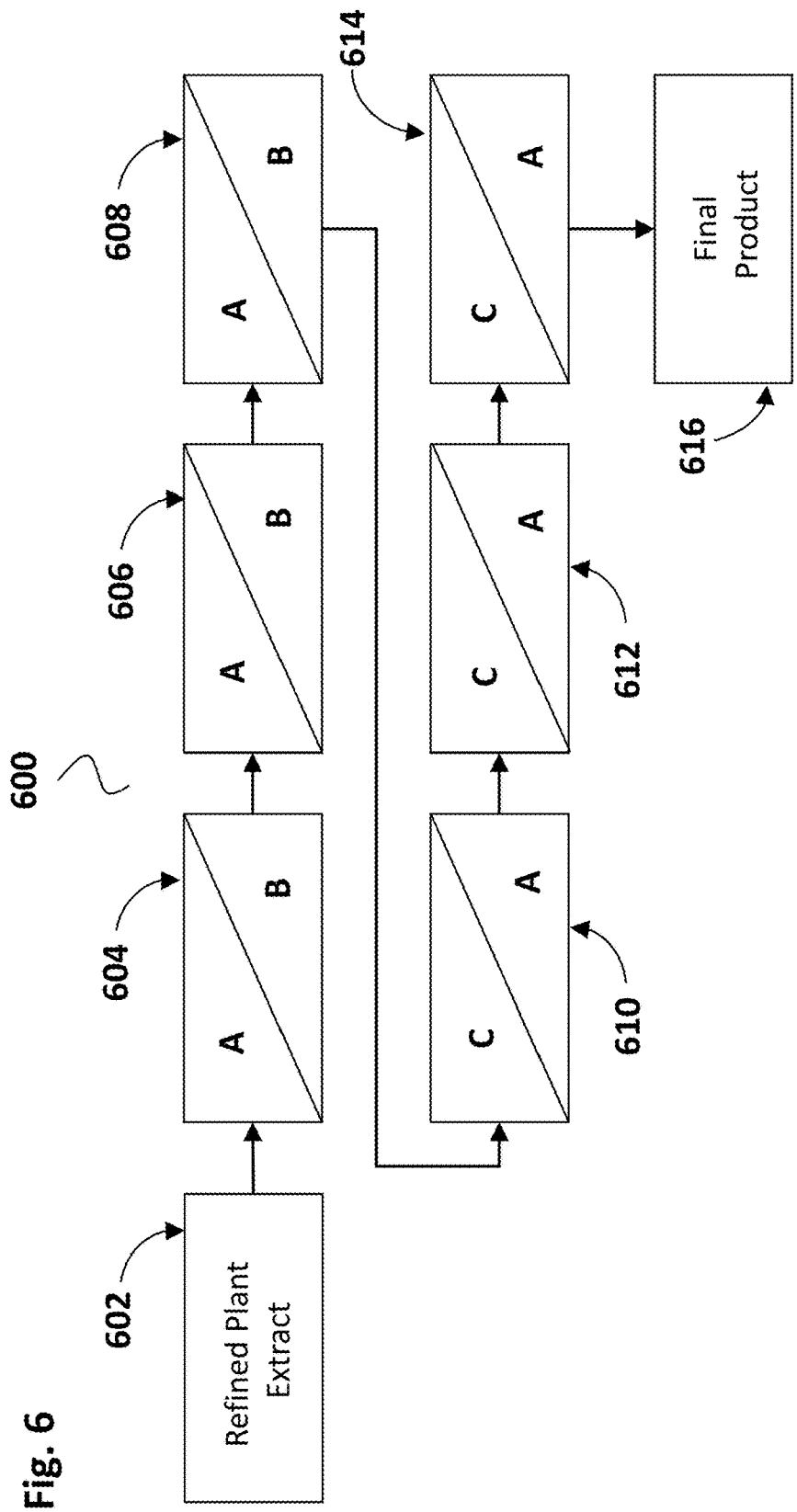
FIG. 6 shows a fifth process to remove unwanted solvent residue from a de-sugared phytocannabinoid rich oil intermediary involving a series of rotovaping operations using a first solvent A in a first series of steps, followed by using a second solvent C in a subsequent series of steps.

FIG. 6 shows a fifth optional process, being a solvent removal process 600 to remove unwanted solvent residue from a de-sugared phytocannabinoid rich oil intermediary, a refined plant extract 602, or a material derived from one or more of the preceding inventive treatment steps described herein. In one embodiment of a solvent removal process 600, a plurality of individual rotovaping operations is considered to progressively reduce the amount of undesired residual solvents present, targeting both hydrophilic and hydrophobic solvents. In this present embodiment, a series of three independent rotovating operations, 604, 606 and 608 are shown involving a series of rotovaping operations using a first moderate E° value solvent as a removal aid, such as for example ethanol, which is added to the PCR oil intermediary refined plant extract 602 in a first addition step 604A, at an approximate ratio of from between 1:4 to 4:1 (v/v), or alternatively from 1:3 to 3:1 (v/v) or alternatively from 1:2 to 2:1 (v/v) with respect to ratio of PCR oil intermediary refined plant extract 602 to removal aid. Once mixed in step 604A, the rotovaping operation, 604B is commenced and continued until a predetermined amount of the first aliquot of removal aid is recovered, for example, being 50%, or alternatively 75%, or alternatively 85%, or alternatively 95% of the original volume of said first moderate E° value solvent employed. This first step 604 is then repeated with a second rotovaping step 606, using a second aliquot of the same solvent used prior, a fresh aliquot being added to the rotavapor in step 606A, and the rotovaping operation, 606B being commenced and continued until the predetermined amount of the second aliquot of removal aid is recovered, this amount being the same or different from that selected as an end point of the preceding rotovaping operation 604. Following the second rotovaping process 606, a third optional rotovaping process 608 can be completed in a similar manner to the second process 606, or varied as desired in regard to the choice of solvent used, or rotovaping conditions employed, in order to achieve the greatest reduction in the amount of undesired hydrophilic and alkanol soluble or miscible solvents, in a first set of one or a plurality of rotovaping steps 604, 606, 608 using a first low E° solvent as a removal aid.

In this present embodiment as illustrated in FIG. 6, a second set of a series of three independent rotovating operations, 610, 612 and 614 are shown involving a series of rotovaping operations using a second, very low E° value solvent as a second removal aid, such as for example water, which is added to the PCR oil intermediary derived from any one of preceding rotovaping steps 604, 606 or 608. In this embodiment, the second removal aid may be added to the residue present in the rotavapor following the first set of rotovaping operations shown, in addition step 610C, at an approximate ratio of from between 1:4 to 4:1 (v/v), or alternatively from 1:3 to 3:1 (v/v) or alternatively from 1:2 to 2:1 (v/v) with respect to ratio of the volumes of PCR oil intermediary refined plant extract 602 to removal aid. Once mixed or adequately dispersed into the water in step 610C, the rotovaping operation, 610A is commenced and continued until a predetermined amount of the first aliquot of the second removal aid (water) is recovered, for example, being 50%, or alternatively 75%, or alternatively 85%, or alternatively 95% of the original volume of solvent employed. The step 610 is then repeated with a subsequent rotovaping step 612, using a second aliquot of the same solvent used prior, a fresh aliquot being added to the rotavapor in step 612C, and the rotovaping operation 612A being commenced and continued until the predetermined amount of the second aliquot of removal aid is recovered, this amount being the same or different from that selected as an end point of the preceding rotovaping operation 610. Following rotovaping step 612, another, optional, rotovaping step 614 can be completed in a similar manner as to either the preceding step 610 or step 612, or varied as desired in regard to the choice of solvent used, or rotovaping conditions employed, in order to achieve the greatest reduction in the amount of undesired hydrophobic and water immiscible solvents present. In the embodiment shown in FIG. 6, a final product 616 is obtained after completing at least one hydrophilic solvent removal step 604 and at least one hydrophobic solvent removal step 610, wherein the final product 616 is a condensed high content PCR oil with high CBD content free of undesired amounts of extraction and process solvents previously introduced or used in any one or more of the disclosed inventive processing steps herein. In further embodiments, only one rotovaping step 604 and one rotovaping step 610 need to be completed, or alternatively only two of a first series of rotovaping steps 604 and 606, followed by a second series of rotovaping steps 610 and 612.

In selected embodiments, the rotavapors are operated for about 1 hour for each individual step, at a temperature of between 50-90° C., at a reduced pressure of between 10-100 torr, and is considered to be complete when no additional condensation of recovered solvent is observed after between about 5-10 minutes. In embodiments employing hexane or similar hydrocarbon solvents, a low temperature of between 50-80° C., or alternatively between 40-60° C. can be employed, while for embodiments employing ethanol or water, a higher temperature of between 60-90° C., or alternatively between 70-80° C. is more suitable employed to remove the most solvent.

Various commercial-sized rotavapors are available and suitable for use in embodiments of the invention as disclosed, including for example, but not limited to the Buchi Rotavapor® R-Series, available with a recirculating chiller (Chiller F-325), from BUCHI Corporation, 19 Lukens Drive, Suite 400, DE 19720 New Castle, USA, the Heidolph large scale evaporators of the Hei-VAP Industrial series, available from Heidolph North America, 1241 Jarvis Ave., Elk Grove Village, Ill. 60007, USA, and the EcoVap RE-7 series large-scale rotary evaporators available from Hydrion Scientific Instruments, 760 W 40th Street, Baltimore, Md. 21210 USA.

Experimental Example

In one example embodiment, an extraction process was performed according to the present disclosure, starting with approximately 150 kg of hemp material derived from a mixed source of *C. sativa* and *C. indica* plants, including flowers, seeds and stems, being ground and macerated to produce a hemp material that was a coarse, flaky powder, slightly sticky in texture and dark green in appearance. The hemp material was then saturated with 450 L of pure ethanol (roughly 3:1 material ratio) in a 1000 L tote and the mixture stirred for approximately 3 hours. The mixture was then filtered into a second 1000 L tote by means of decanting to isolate settled material and subsequent filtering of the liquor using a 100 micron filter. A second aliquot of between 300 to 500 L of pure ethanol was then added to the residual plant material remaining from the first extraction, and the process repeated. After two repeated iterations, approximately 1000 L of solution was obtained, having successfully extracted between about 80-90% of the available cannabinoids originally present in the starting hemp material, as determined by analysis. In this example embodiment, a subsequent distillation step was not performed, as the total volume of extract recovered was a manageable quantity. In related embodiments at larger production scales, a subsequent distillation step may be performed in order to remove some of the extraction solvents employed, and to concentrate the active materials for easier handling in subsequent process steps.

Returning to the first example embodiment, the next step was to perform the decolorization and dewaxing operations. Here, the extract was passed through a 24"×72" (width× height) column filled with a mixture of two types of carbon, TOG and Centaur. While the TOG media serves as the primary absorption media (owing to it's greater combined surface area per unit weight) in this example embodiment, the Centaur media acts, in addition to its function as an absorption media, to help reduce the back pressure inside the column as it is granular in nature and has a larger average particle size distribution greater than the TOG media, thus helping to decrease the overall packing density of the column with combined media present. This example filtration and absorption step was repeated an additional number of times, noting that effective decolorization tended to occur within the first and/or second pass, while effective dewaxing is achieved after a second and/or third pass of the filtrate solution through the column material. In related embodiments, a fresh filter media can be prepared and utilized for second and/or third filtration steps, although the same filtrate can also be used repeatedly until its effectiveness is seen to decrease. In related embodiments, as column media gets used and ages, they continue to be most effective for use in the first decolorization step even as they lose efficacy in their ability to dewax. Accordingly, in related embodiments, the order of use and recycling of columns using previously used filter media can be orchestrated in use by employing media that has already lost its desired dewaxing efficacy in an either treatment step for initial decolorization of the hemp material extract.

After the decolorization and dewaxing process has been performed to satisfaction, the volume of extract is typically found to have decreased, due to loses of the solvent carrier to column wetting and some retention of active material within the column, and experimental losses from handling, decanting, pumping and other void volumes lost, at least in batch mode embodiments of the present invention. The decolorized and dewaxed extract is then treated to remove THC. Returning again to this example embodiment, the approximately 1000 L of extract recovered from the first extraction process was mixed with water sufficient (about 250 L) to produce a diluted, roughly 80:20 v/v solution, reducing the effective CBD level to about 4.0 wt., and then passed through a third column, again using a 24"×72" (width×height) column filled with a mixture of two types of carbon, TOG and Centaur, but arranged in a layered pattern similar to that shown in the inventive embodiment in FIG. 4. In this step of the example embodiment, a layered column was first prepared by adding the coarser Centaur material as a bottom bed material, roughly 25% of the available column volume, followed by addition of the finer TOG material in roughly 50% volume, with the final 25% of the column topped with Centaur granulated activated carbon. The resulting filtrate obtained was analyzed and found to have no detectable THC or THCA components present within the experimental limit of 0.01 wt %, thus successfully achieving effective removal of the psychoactive components initially present. In addition, this and other embodiments of the inventive THC extraction step also appear to remove or reduce the quantity of other undesirable components present, such as for example, but not limited to *Cannabis* terpenes, flavonoids, lipids and other medium sized molecular weight and less water soluble molecular species. In a final step of this example embodiment of the inventive THC removal process, the recovered filtrate was then distilled, resulting in the recovering of an oil that was analyzed to have a content of about 80% CBD.

In this example experimental embodiment, the concentrated oil obtained from the decolorization and dewaxing process was then treated to remove sugar, starting first with the addition of hexane in a 7:1 (v/v) ratio. This hexane:extract ratio is optimized to maximize the collective CBX component solubility (and minimize their precipitation) while minimizing sugar solubility (and maximize its precipitation). The sugars were observed to be precipitated and settled after about 12 hours, forming a hard, compacted mass at the bottom of the treatment vessel. Because the CBX-containing hexane layer can be decanted from the top, the solubilized CBX hexane solution is easily separated and was then introduced into one or more 50 L rotary evaporators for the subsequent solvent removal process.

To remove hexane, the decanted hexane solution was rotovaped (distilled) to a point at which no more hexane was recovered, and then 1 L of ethanol was added to the concentrated CBX extract. Since hexane is miscible with ethanol to some extent, it tends to displace any residual hexane in to the vapor phase and allows the remaining traces to be removed from the oil. Two more additions of 1 L each of ethanol was then performed, to a point at which no more hexane condensation on the cooling tower was observed, indicating that as much hexane solvent was removed as possible between the ethanol dilution and distillation steps. This process was then repeated with water (in additions of 1 L each, three additions) to now remove the ethanol solvent from the oil. The rotovaping conditions employed were approximately 1 hour at a temperature of 60° C. at a reduced pressure of about 20 torr for the first set of operations to remove hexane, followed by approximately 1 hour at a temperature of 80° C. at a reduced pressure of about 20 torr for the second set of operations to remove ethanol.

Following this last process, a highly concentrated CBX oil was obtained, analyzed to contain resulting in the isolation of approximately 45 L of a dark red, flowing oil extract that upon analysis, showed a PCR oil content of 85 wt./vol. %, having a total CBX combined concentration of 75 wt. %, the balance of the composition being ethanol, without any detectable level of either THC or THCA, the latter components, if present, being below the analytical detection limit of 0.01 wt. % as actives. Further, analysis of the final purified extract also confirmed the absence of any detectable heavy metals including lead (Pb) and arsenic (Ar).

Extraction and Process Solvents

Various compositions may be formulated depending on solvent choice and extraction time. While ethanol is generally preferred for therapeutic applications, other solvents that may be of use in various formulations and applications include acetone, acetonitrile, benzene, butanols, chloroform, cyclohexane, 1,2-dichloroethane, dichloromethane, diethyl ether, N,N-dimethylformamide, ethyl acetate, hexane, isopropanol, methanol, methylbutyl ketone, methylcyclohexane, pentane, propanols, tetrahydrofuran, toluene, and xylene and the other solvents and solvent systems known to the art. If ethanol is utilized as the extraction solvent, anhydrous absolute (200 proof) alcohol is preferable to 95% (190 proof). A non-denatured ethanol is preferable. If a denatured alcohol is utilized, a denaturant such as methanol or other substance with a boiling point lower than ethanol is preferred, and removal of said denaturant is generally achieved through one or more embodiments of the extraction and isolation processes and/or steps as described herein. The choice of solvent also depends on the final residual levels, which are desirably reduced to a level that is not regulated under United States Pharmacopeia exposure limits, as shown in Table 1 below.

TABLE 1

Acceptable Residual Solvent Levels

| Solvent | Solvent Class(1) | PDE (mg/day)(2) | Concentration Limit (ppm)(3) |
|---|---|---|---|
| Pentane | 3 | 50 | 5000 |
| Hexane | 2 | 2.9 | 290 |
| Cyclohexane | 2 | 38.8 | 3880 |
| Heptane | 3 | 50 | 5000 |
| Methanol | 2 | 30 | 3000 |
| Ethyl Ether | 3 | 50 | 5000 |
| Ethanol(4) | 3 | 50 | 5000 |

Notes:
(1)Solvents in Hazard Class 1 are known human carcinogens with environmental hazards. Hazard Class 2 are non-genotoxic animal carcinogens or possible causative agents with irreversible toxicity, neurotoxic or teratogenicity with significant but reversible toxicities. Hazard Class 3 have low toxic potential; no health-based exposure limit is needed.
(2)PDE is the limit of material associated with a safe exposure limit or tolerable daily intake level designated as the Permitted Daily Exposure for an adult male by the World Health Organization. Source: United States Pharmacopeia, General Addition, Volume 30, Chemical Tests, Residual Solvents, Chapter 467, p. 1-10. (USA).
(3)Acceptable concentration limit in a pharmaceutical product formulation, based on a unit dosage of 10 grams and related to PDE by: Concentration (ppm) = 1000 × PDE/(1 unit dose).
(4)Levels of ethanol are permitted to exceed this value, but require labelling indicative of the amount present.

One having skill in the art will appreciate that the various embodiments of the invention disclosed herein may be performed in a variety of ways, employing a variety of means known in the art to achieve the object of the invention, and that the various extraction and isolation processes and steps thereof, may be performed in different orders, using different materials and techniques from those disclosed herein serving only as representative examples, and that the order of some of the processes and steps may be varied, or some skipped if warranted by the nature and/or source of starting material to be treated according to one or more of the inventive methods described above.

The above illustration provides many different embodiments or embodiments for implementing different features of the invention. Specific embodiments of components and processes are described to help clarify the invention. These are, of course, merely embodiments and are not intended to limit the invention from that described in the claims.

Although the invention is illustrated and described herein as embodied in one or more specific examples, it is nevertheless not intended to be limited to the details shown, since various modifications and structural changes may be made therein without departing from the spirit of the invention and within the scope and range of equivalents of the claims. Accordingly, it is appropriate that the appended claims be construed broadly and in a manner consistent with the scope of the invention, as set forth in the following claims.

What is claimed is:

1. A process for making THC free decolorized phytocannabinoid rich oil from a hemp extract consisting essentially of:

a. a first extraction process employing a step of solvent extraction of plant components from a macerated hemp plant material, followed by a distillation step to provide a first phytocannabinoid rich oil that is free from excess solvents; wherein said first extraction solvent is selected from acetonitrile, benzene, butanol, chloroform, cyclohexane, 1,2-dichloroethane, dichloromethane, diethyl ether, N,N-dimethylformamide, ethyl acetate, hexane, methylbutyl ketone, methylcyclohexane, pentane, propanol, tetrahydrofuran, toluene, and xylene wherein said hemp has a sugar:wax ratio exceeding 1:1;

b. a decolorization and dewaxing process employing the steps of diluting said first phytocannabinoid rich oil in a mixed Kb solvent to form a mixture and then treating said mixture by means of a series of at least one of a plurality of filtration steps to remove plant chlorophylls and waxes; wherein said first filtration step provides the effective removal of chlorophyll and said subsequent second, or alternatively third of said plurality of filtration steps provides the effective removal of wax components resulting in a second decolorized phytocannabinoid rich oil; wherein said first filtration step consists essentially of passing said first phytocannabinoid rich oil through a filter media selected from the group consisting of activated carbon, carbon, clay, alumina, alumina-activated clay, cellulose, sand, silica, diatomaceous earth, carbonate, granite and quartz, zeolites, synthetic polymers, synthetic copolymers, synthetic resins, synthetic gels, and mixtures thereof;

c. a THC removal process employing the step of treating said second decolorized phytocannabinoid rich oil by means of a THC extraction step; wherein said THC extraction step consists essentially of passing said second decolorized phytocannabinoid rich oil through a fourth filter media; wherein said fourth filter is a mixture of at least two different particle size filter materials; wherein said third THC removal process results in the recovery of a third THC free decolorized phytocannabinoid rich oil; wherein said mixture consist of a heterogeneous mixture of two or more filter media or a layered construct thereof; wherein said filter media is selected from activated carbon, carbon, clay, alumina, alumina-activated clay, cellulose, sand, silica, diatomaceous earth, carbonate, granite and quartz, zeolites, synthetic polymers, synthetic copolymers, synthetic resins, synthetic gels, and mixtures thereof;

d. a sugar removal process employing the steps of a first, primary distillation of said third THC free decolorized phytocannabinoid rich oil, followed by a subsequent dilution step of the recovered distillate of said first primary distillation with a hydrophobic solvent; a subsequent precipitation step to remove precipitated sugars to produce an intermediate sugar-free extract; followed by a second, secondary distillation of said intermediate extract to produce a concentrated sugar and THC free decolorized phytocannabinoid rich oil; and e. a solvent reduction process employing the steps of first diluting said concentrated sugar and THC free decolorized phytocannabinoid rich oil using a first solvent in a primary series of rotovaping operations; followed by using a second solvent in a secondary series of rotovaping operations to produce a solvent-free, concentrated sugar and THC free decolorized phytocannabinoid rich oil; wherein said first and second series of said rotovaping operations each involves the step of heating and solvent removal under reduced atmospheric pressure until a point is reached in which no additional solvent condensation is observed, wherein said solvents are selected from the group consisting of acetonitrile, benzene, butanol, chloroform, cyclohexane, 1,2-dichloromethane, dichloromethane, diethyl ether, N,N-dimethylformamide, ethyl acetate, hexane, methylbutyl, ketone, methylcyclohexane, pentane, propanol, tetrahydrofuran, toluene, and xylene.

2. A process for making THC free decolorized phytocannabinoid rich oil from a hemp extract, the process comprising:

a. an extraction process employing a step of solvent extraction of plant components from a macerated hemp plant material, followed by a distillation step to provide a first phytocannabinoid rich oil that is free from excess solvents; wherein said extraction solvent is selected from acetonitrile, benzene, butanol, chloroform, cyclohexane, 1,2-dichloroethane, dichloromethane, diethyl ether, N,N-dimethylformamide, ethyl acetate, hexane, methylbutyl ketone, methylcyclohexane, pentane, propanol, tetrahydrofuran, toluene, and xylene wherein said hemp has a sugar:wax ratio exceeding 1:1;

b. a decolorization and dewaxing process employing the steps of diluting said first phytocannabinoid rich oil in a mixed Kb solvent to form a mixture and then treating said mixture by means of a series of at least one of a plurality of filtration steps to remove plant chlorophylls and waxes; wherein one filtration step provides the effective removal of chlorophyll and another filtration step provides the effective removal of wax components resulting in a second decolorized phytocannabinoid rich oil; wherein said first filtration step comprises passing said first phytocannabinoid rich oil through a filter media selected from the group consisting of activated carbon, carbon, clay, alumina, alumina-activated clay, cellulose, sand, silica, diatomaceous earth, carbonate, granite and quartz, zeolites, synthetic polymers, synthetic copolymers, synthetic resins, synthetic gels, and mixtures thereof;

c. a THC removal process employing the step of treating said second decolorized phytocannabinoid rich oil by means of a THC extraction step; wherein said THC extraction step comprises passing said second decolorized phytocannabinoid rich oil through a fourth filter media; wherein said fourth filter is a mixture of at least two different particle size filter materials; wherein said third THC removal process results in the recovery of a third THC free decolorized phytocannabinoid rich oil; wherein said mixture comprises a heterogeneous mixture of two or more filter media or a layered construct thereof; wherein said filter media is selected from activated carbon, carbon, clay, alumina, alumina-activated clay, cellulose, sand, silica, diatomaceous earth, carbonate, granite and quartz, zeolites, synthetic polymers, synthetic copolymers, synthetic resins, synthetic gels, and mixtures thereof;

d. a sugar removal process employing the steps of a first, primary distillation of said third THC free decolorized phytocannabinoid rich oil, followed by a subsequent dilution step of the recovered distillate of said first primary distillation with a hydrophobic solvent; a subsequent precipitation step to remove precipitated sugars to produce an intermediate sugar-free extract; followed by a second, secondary distillation of said intermediate extract to produce a concentrated sugar and THC free decolorized phytocannabinoid rich oil; and e. a solvent reduction process employing the steps of first diluting said concentrated sugar and THC free decolorized phytocannabinoid rich oil using a first solvent in a primary series of rotovaping operations; followed by using a second solvent in a secondary series of rotovaping operations to produce a solvent-free, concentrated sugar and THC free decolorized phytocannabinoid rich oil; wherein said first and second series of said rotovaping operations each involves the step of heating and solvent removal under reduced atmospheric pressure until a point is reached in which no additional solvent condensation is observed, wherein said solvents are selected from the group consisting of acetonitrile, benzene, butanol, chloroform, cyclohexane, 1,2-dichloromethane, dichloromethane, diethyl ether, N,N-dimethylformamide, ethyl acetate, hexane, methylbutyl, ketone, methylcyclohexane, pentane, propanol, tetrahydrofuran, toluene, and xylene.

3. The process of claim 2, wherein said concentrated sugar and THC free decolorized phytocannabinoid rich oil is free of analytically detectable levels of pesticides, fungicides and heavy metals.

4. The process of claim 2, wherein said concentrated sugar and THC free decolorized phytocannabinoid rich oil contains not less than 80 wt./vol.% of CBX materials selected from cannabidiol (CBD), cannabidiolic acid (CBDA), cannabinol (CBN), cannabichromene (CBC), cannabigerol (CBG), cannabigerovarin (GBGV), cannabinidiol (CBND), cannabicyclol (CBL), cannabichromevarin (CBCV), cannabidivarin (CBDV) and cannabigerol monomethyl ether (CBGM), and other hemp plant essential oils;
and wherein levels of tetrahydrocannabinol (THC), tetrahydrocannbinolic acid (THCA) and tetrahydrocannabinovarin (THCV) are each below 0.3 wt./vol.%.

5. The process of claim 2, wherein said concentrated sugar and THC free decolorized phytocannabinoid rich oil contains not less than 85 wt./vol.% of CBX materials selected from cannabidiol (CBD), cannabidiolic acid (CBDA), cannabinol (CBN), cannabichromene (CBC), cannabigerol (CBG), cannabigerovarin (GBGV), cannabinidiol (CBND), cannabicyclol (CBL), cannabichromevarin (CBCV), cannabidivarin (CBDV) and cannabigerol monomethyl ether (CBGM), and other hemp plant essential oils; and wherein levels of tetrahydrocannabinol (THC), tetrahydrocannbinolic acid (THCA) and tetrahydrocannabinovarin (THCV) are all below 0.1 wt./vol.%.

6. The process of claim 2, wherein said concentrated sugar and THC free decolorized phytocannabinoid rich oil is free of visible chlorophyll; wherein said phytocannabinoid rich oil is free of measurable quantities of wax; and wherein said phytocannabinoid rich oil is a stable, homogenous solution free of suspended solids and free of analytically detectable levels of pesticides, fungicides and heavy metals.

7. The process of claim 1, wherein said concentrated sugar and THC free decolorized phytocannabinoid rich oil is free of analytically detectable levels of pesticides, fungicides and heavy metals.

8. The process of claim 1, wherein said concentrated sugar and THC free decolorized phytocannabinoid rich oil contains not less than 80 wt./vol.% of CBX materials selected from cannabidiol (CBD), cannabidiolic acid (CBDA), cannabinol (CBN), cannabichromene (CBC), cannabigerol (CBG), cannabigerovarin (GBGV), cannabinidiol (CBND), cannabicyclol (CBL), cannabichromevarin (CBCV), cannabidivarin (CBDV) and cannabigerol monomethyl ether (CBGM), and other hemp plant essential oils, and wherein levels of tetrahydrocannabinol (THC), tetrahydrocannbinolic acid (THCA) and tetrahydrocannabinovarin (THCV) are each below 0.3 wt./vol.%.

9. The process of claim 1, wherein said concentrated sugar and THC free decolorized phytocannabinoid rich oil contains not less than 85 wt./vol.% of CBX materials selected from cannabidiol (CBD), cannabidiolic acid (CBDA), cannabinol (CBN), cannabichromene (CBC), cannabigerol (CBG), cannabigerovarin (GBGV), cannabinidiol (CBND), cannabicyclol (CBL), cannabichromevarin (CBCV), cannabidivarin (CBDV) and cannabigerol monomethyl ether (CBGM), and other hemp plant essential oils, and wherein levels of tetrahydrocannabinol (THC), tetrahydrocannbinolic acid (THCA) and tetrahydrocannabinovarin (THCV) are all below 0.1 wt./vol.%.

10. The process of claim 1, wherein said concentrated sugar and THC free decolorized phytocannabinoid rich oil is free of visible chlorophyll, wherein said phytocannabinoid rich oil is free of measurable quantities of wax, and wherein said phytocannabinoid rich oil is a stable, homogenous solution free of suspended solids and free of analytically detectable levels of pesticides, fungicides and heavy metals.

11. The process of claim 3, wherein said concentrated sugar and THC free decolorized phytocannabinoid rich oil contains not less than 80 wt./vol.% of CBX materials selected from cannabidiol (CBD), cannabidiolic acid (CBDA), cannabinol (CBN), cannabichromene (CBC), cannabigerol (CBG), cannabigerovarin (GBGV), cannabinidiol (CBND), cannabicyclol (CBL), cannabichromevarin (CBCV), cannabidivarin (CBDV) and cannabigerol monomethyl ether (CBGM), and other hemp plant essential oils, and wherein levels of tetrahydrocannabinol (THC), tetrahydrocannbinolic acid (THCA) and tetrahydrocannabinovarin (THCV) are each below 0.3 wt./vol.%.

12. The process of claim 3, wherein said concentrated sugar and THC free decolorized phytocannabinoid rich oil contains not less than 85 wt./vol.% of CBX materials selected from cannabidiol (CBD), cannabidiolic acid (CBDA), cannabinol (CBN), cannabichromene (CBC), cannabigerol (CBG), cannabigerovarin (GBGV), cannabinidiol (CBND), cannabicyclol (CBL), cannabichromevarin (CBCV), cannabidivarin (CBDV) and cannabigerol monomethyl ether (CBGM), and other hemp plant essential oils; and wherein levels of tetrahydrocannabinol (THC), tetrahydrocannbinolic acid (THCA) and tetrahydrocannabinovarin (THCV) are all below 0.1 wt./vol.%.

13. The process of claim 6, wherein said concentrated sugar and THC free decolorized phytocannabinoid rich oil contains not less than 80 wt./vol.% of CBX materials selected from cannabidiol (CBD), cannabidiolic acid (CBDA), cannabinol (CBN), cannabichromene (CBC), cannabigerol (CBG), cannabigerovarin (GBGV), cannabinidiol (CBND), cannabicyclol (CBL), cannabichromevarin (CBCV), cannabidivarin (CBDV) and cannabigerol monomethyl ether (CBGM), and other hemp plant essential oils;
and wherein levels of tetrahydrocannabinol (THC), tetrahydrocannbinolic acid (THCA) and tetrahydrocannabinovarin (THCV) are each below 0.3 wt./vol.%.

14. The process of claim 6, wherein said concentrated sugar and THC free decolorized phytocannabinoid rich oil contains not less than 85 wt./vol.% of CBX materials selected from cannabidiol (CBD), cannabidiolic acid (CBDA), cannabinol (CBN), cannabichromene (CBC), cannabigerol (CBG), cannabigerovarin (GBGV), cannabinidiol (CBND), cannabicyclol (CBL), cannabichromevarin (CBCV), cannabidivarin (CBDV) and cannabigerol monomethyl ether (CBGM), and other hemp plant essential oils;

and wherein levels of tetrahydrocannabinol (THC), tetrahydrocannbinolic acid (THCA) and tetrahydrocannabinovarin (THCV) are all below 0.1 wt./vol.%.

15. The process of claim 2, wherein said concentrated sugar and THC free decolorized phytocannabinoid rich oil is free of visible chlorophyll.

16. The process of claim 15, wherein said concentrated sugar and THC free decolorized phytocannabinoid rich oil contains not less than 80 wt./vol.% of CBX materials selected from cannabidiol (CBD), cannabidiolic acid (CBDA), cannabinol (CBN), cannabichromene (CBC), cannabigerol (CBG), cannabigerovarin (GBGV), cannabinidiol (CBND), cannabicyclol (CBL), cannabichromevarin (CBCV), cannabidivarin (CBDV) and cannabigerol monomethyl ether (CBGM), and other hemp plant essential oils; and wherein levels of tetrahydrocannabinol (THC), tetrahydrocannbinolic acid (THCA) and tetrahydrocannabinovarin (THCV) are each below 0.3 wt./vol.%.

17. The process of claim 15, wherein said concentrated sugar and THC free decolorized phytocannabinoid rich oil contains not less than 85 wt./vol.% of CBX materials selected from cannabidiol (CBD), cannabidiolic acid (CBDA), cannabinol (CBN), cannabichromene (CBC), cannabigerol (CBG), cannabigerovarin (GBGV), cannabinidiol (CBND), cannabicyclol (CBL), cannabichromevarin (CBCV), cannabidivarin (CBDV) and cannabigerol monomethyl ether (CBGM), and other hemp plant essential oils; and wherein levels of tetrahydrocannabinol (THC), tetrahydrocannbinolic acid (THCA) and tetrahydrocannabinovarin (THCV) are all below 0.1 wt./vol.%.

* * * * *